United States Patent [19]

Wood

[11] Patent Number: Plant 6,699

[45] Date of Patent: Mar. 28, 1989

[54] BLUEBERRY—VARIETY NUI

[75] Inventor: Franklin H. Wood, Hamilton, New Zealand

[73] Assignee: Maftech North, Ruakura Agricultural Research Centre, Hamilton, New Zealand

[21] Appl. No.: 101,954

[22] Filed: Sep. 28, 1987

[30] Foreign Application Priority Data

Sep. 29, 1986 [NZ] New Zealand ..... PV 3-50-1

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Abelman Frayne Rezac & Schwab

[57] ABSTRACT

A blueberry plant which bears large fruit early in the season.

4 Drawing Sheets

In 1969, seed from a range of blueberry crosses was gifted to Ruakura as a result of an agreement between P. Bates (Ruakura) and A. D. Draper (USDA). The NZ objective was to identify plant material which was more suitable for local conditions. Over a thousand seedlings were initially screened in the first stage evaluation from which forty seedling types were identified as promising. Closer critical examination of these seedlings over several years, resulted in the selection of ten elite types. Seven of these ten seedlings had Earliblue, Blue-crop parentage and characteristically produced early maturing, high quality fruit. The remainder had Berkeley and Blueray parentage and typically produced later maturing fruit. These elite seedlings were planted out in 1982 in a fully replicated trial to determine their commercial usefulness. Puru, Nui and Reka, three elite Ruakura selections, are chance seedlings arising from Earliblue and Bluecrop crosses. They are the product of careful screening and evaluation which has taken place over many years.

COMPARISON OF NUI AND SIMILAR VARIETIES

Nui is very similar to Puru in many respects; however, fundamental physical and physiological differences set them apart as two distinct cultivars. These differences include stem, blossom and fruit characteristics (see detailed descriptions), as well as agronomic differences. For example, Puru typically produces pubescent yellow-green stems while those produced by Nui are completely smooth. Puru produces white, elongated (cylindraceous) flowers with a faint pink blush, while Nui has more rounded flowers (urceolate) and a more pronounced pink blush.

Differences between Nui and the five standard varieties — Earliblue, Collins, Stanley, Bluecrop and Darrow — are numerous and therefore are outlined in Tables 1–5. Tables 1 and 5 summarise the main points of similarities and differences while Tables 2–4 summarise agronomic details.

FIGS. 1 and 2 illustrate the seasonal nature of fruit production and associated yields in relation to other cultivars, while FIGS. 3–6 provide visual support for the nature of physical differences.

DETAILED DESCRIPTION OF NUI

Seedling reference: No. 12.

Flowering habit: Predominantly white with a medium to strong pink blush, accompanied by darker pink stripes. Flowering takes place during the first or second week of September which is early to mid-season in the Southern Hemisphere and after leaf appearance. Flowers have a more rounded (urceolate) appearance unlike Puru or Reka which are more cylindraceous. The average corolla length is 8 mm.

Cluster: Small, mainly terminal drooping clusters of 4–10 flowers.

Leaves: Deciduous and advanced before flowering. Average length being 84 mm and average width being 57 mm. Leaves slightly pale green and smooth with no accompanying pubescence. Predominantly ovate.

Stems: Smooth stems (glabrous) which are generally light green/yellow when young and turn yellow/-light red with age.

Fruit: Large pale blue fruit produced with a small dry scar, average diameter being 16 mm and average weight 2.1 g. Can exceed fruit size of Puru. Excellent flavour. Calyx partially lobed, loose clustered, medium aroma and low resistance to cracking. Fruit production is early in the season namely late November to early January and mid March to April in the Southern Hemisphere.

Bush habit: Erect spreading, vigorous, more so than Puru.

Propagation: Moderately successful (i.e., easier to propagate than Puru).

TABLE 1

A summary of similarities and differences between Nui and five standard varieties.

| Cultivar | Similarities | Differences* |
|---|---|---|
| Earliblue | flavour<br>early maturing habit<br>berry colour | less bush vigour<br>smaller berry size<br>less precocious<br>larger scar<br>extended harvest |
| Collins | early maturing habit<br>berry colour | less bush vigour<br>smaller berry size<br>less precocious<br>berry firmness<br>larger scar |
| Stanley | early maturing habit<br>bush vigour | smaller berry size<br>less precocious<br>berry flavour<br>berry colour |

TABLE 1-continued

A summary of similarities and differences between Nui and five standard varieties.

| Cultivar | Similarities | Differences* |
|---|---|---|
| Darrow | berry size<br>berry colour<br>bush vigour | later maturing<br>berry flavour<br>extended harvest<br>larger scar |
| Bluecrop | berry colour<br>scar<br>bush vigour | later maturing<br>smaller berry size |

(*cultivar differences with respect to Nui)

TABLE 2

Fruit productionn of three new early Ruakura blueberry selections, Puru, Nui and Reka, and five standard varieties.

| | Yield per season (kg/bush) | | | |
|---|---|---|---|---|
| Cultivar | 1 | 2 | 3 | Year 5 onwards (mean) |
| Earliblue | 0.2 | 0.8 | 1.2 | 2.4 |
| Collins | 0.2 | 0.9 | 1.1 | 1.6 |
| Stanley | 0.3 | 1.1 | 1.9 | 3.1 |
| Bluecrop | 0.1 | 0.5 | 1.4 | 5.8 |
| Darrow | 0.1 | 0.7 | 1.1 | 4.9 |
| Puru | 0.5 | 0.6 | 2.0 | 4.8 |
| Nui | 0.6 | 0.8 | 1.8 | 5.6 |
| Reka | 2.2 | 2.3 | 4.4 | 9.3 |

TABLE 3

Average berry weights of three new early Ruakura selections, Puru, Nui, Reka and five standard varieties.

| Cultivar | Average berry weight (gms) |
|---|---|
| Earliblue | 1.6 |
| Collins | 1.6 |
| Stanley | 1.2 |
| Bluecrop | 1.7 |
| Darrow | 2.0 |
| Puru | 2.2 |
| Nui | 2.1 |
| Reka | 1.6 |

TABLE 4

Pre-Christmas fruit production of three new early varieties, Puru, Nui, Reka and five standard varieties.

| Cultivar | Yield pre-Christmas as a percentage of total production |
|---|---|
| Earliblue | 69 |
| Collins | 82 |
| Stanley | 67 |
| Bluecrop | 55 |
| Darrow | 28 |

TABLE 4-continued

Pre-Christmas fruit production of three new early varieties, Puru, Nui, Reka and five standard varieties.

| Cultivar | Yield pre-Christmas as a percentage of total production |
|---|---|
| Puru | 91 |
| Nui | 88 |
| Reka | 95 |

TABLE 5

General characteristics of three new early Ruakura selections, Puru, Nui, Reka and five standard varieties.

| Cultivar | Season | Bush Growth Habit | Fruit Size | Fruit Colour | Scar |
|---|---|---|---|---|---|
| Earliblue | v. early | moderate spreading | medium-large | light blue | medium/dry |
| Collins | early | moderate spreading | medium | pale blue | medium/dry |
| Stanley | early | vigorous upright | medium-small | pale blue | medium/dry |
| Bluecrop | mid | vigorous upright | medium-large | pale blue | small/dry |
| Darrow | late | vigorous upright | large | pale blue | medium/wet |
| Nui | v. early | vigorous upright | V. large | pale blue | small/dry |
| Puru | v. early | vigorous upright | large | pale blue | small/dry |
| Reka | v. early | vigorous spreading | medium-large | light blue | small/dry |

Additional Notes (i) Leaf measurements were taken on mature leaves and not at the time of full flowering as the leaves at this stage are still expanding.

(ii) Flower numbers vary from 4–10 within a cluster.

(iii) Fruit diameter and weight vary within the season. Early season fruit which is produced on primary whips is much larger and heavier than subsequent fruit produced on secondary and tertiary whips.

(iv) A small autumm crop is produced from mid March onwards. This behaviour is variable and largely depends upon the preceeding dry summer conditions. The small number of fruit produced (in comparison to maincrop) tend to be extremely large.

I claim:

1. A new and distinct variety of blueberry, substantially as herein shown and described, characterised particularly by (a) a high percentage of total yield is produced early in the season, (b) large fruit weight, (c) small dry scar tissue.

* * * * *

FIG. 1 Fruit production season of three new early cultivars Puru, Nui and Reka and five standard varieties.
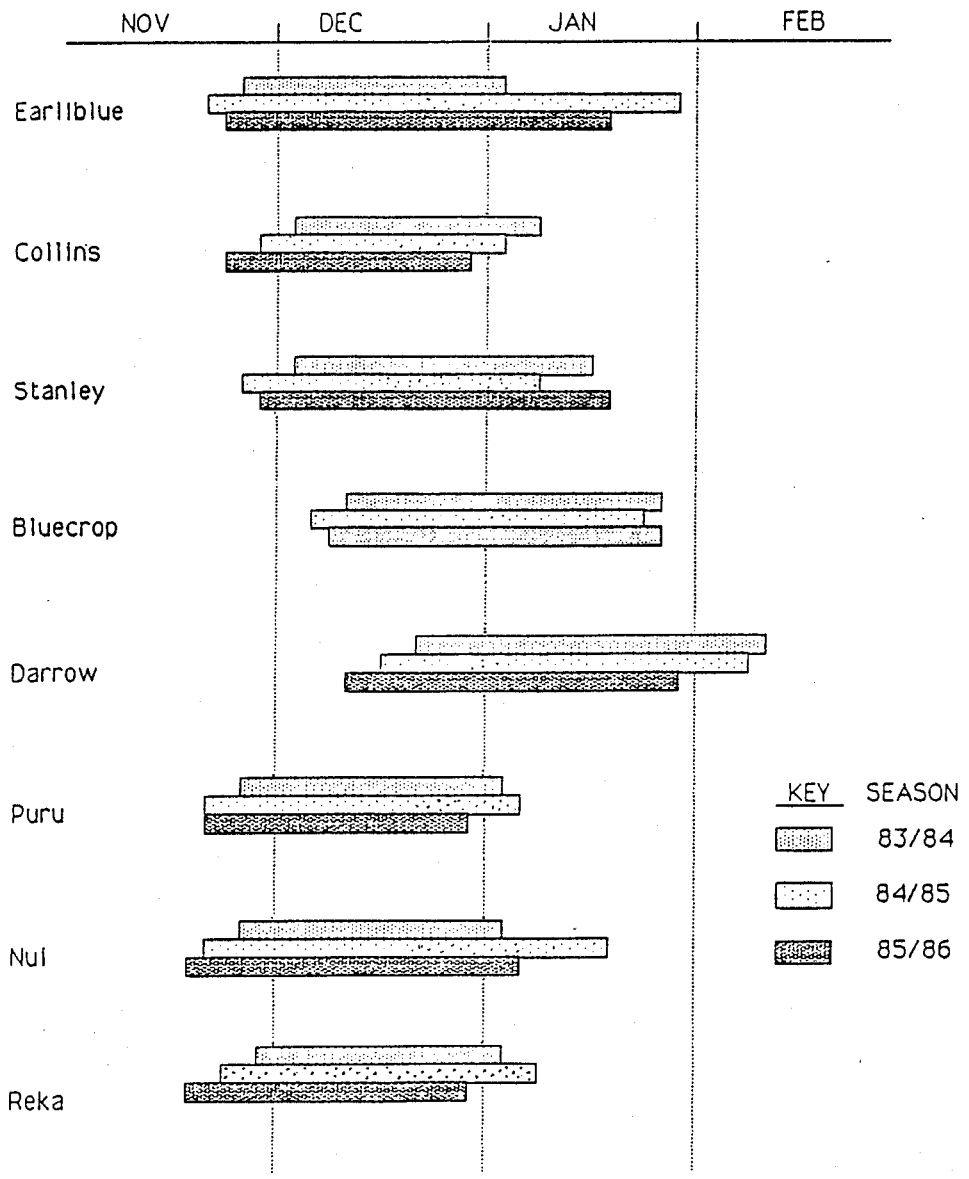

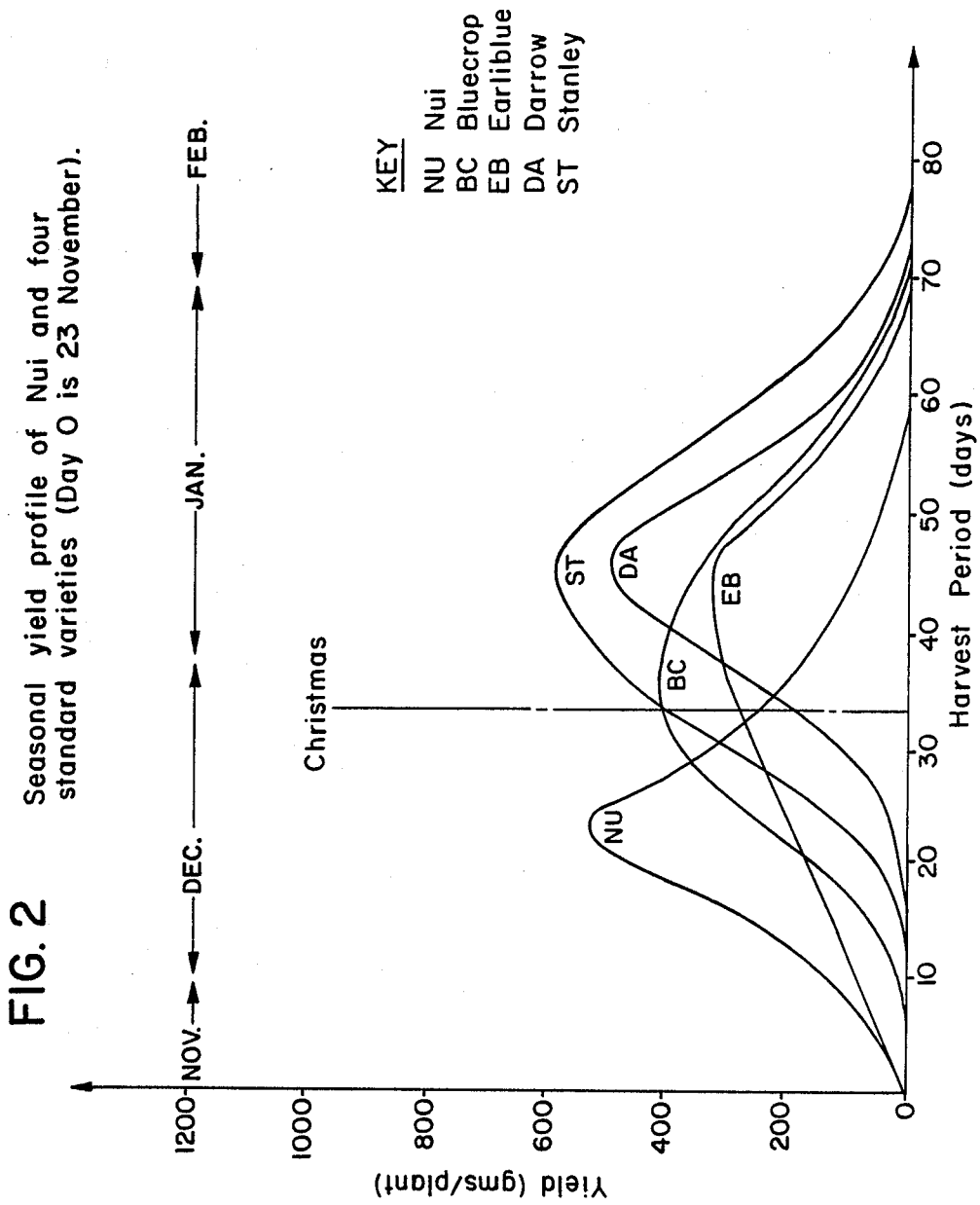
FIG. 2 Seasonal yield profile of Nui and four standard varieties (Day O is 23 November).

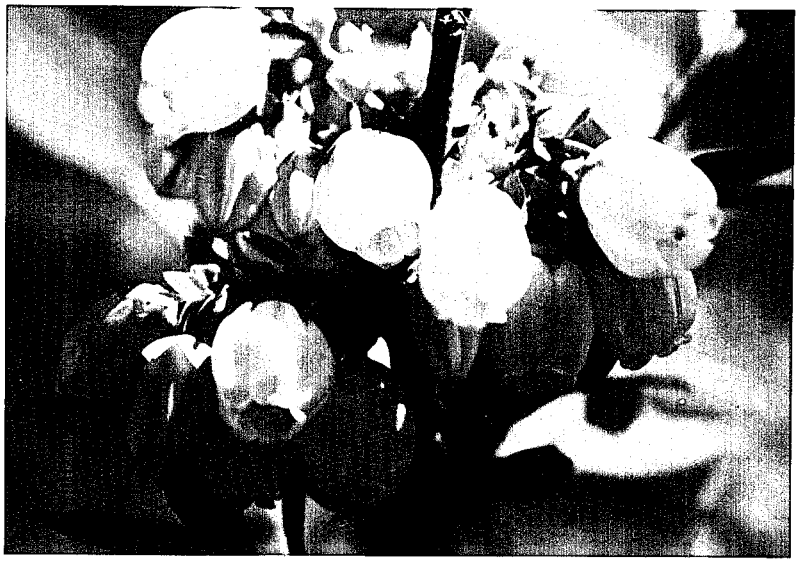
NUI-Floral Development
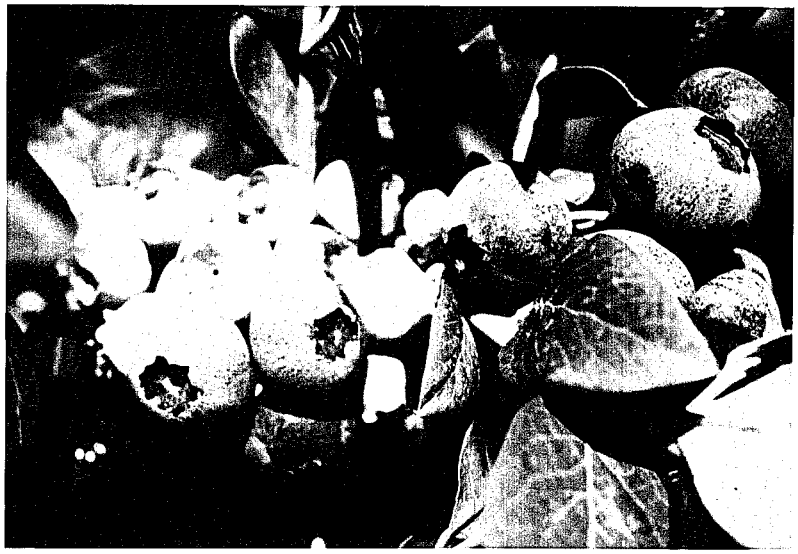
NUI-Fruit Development

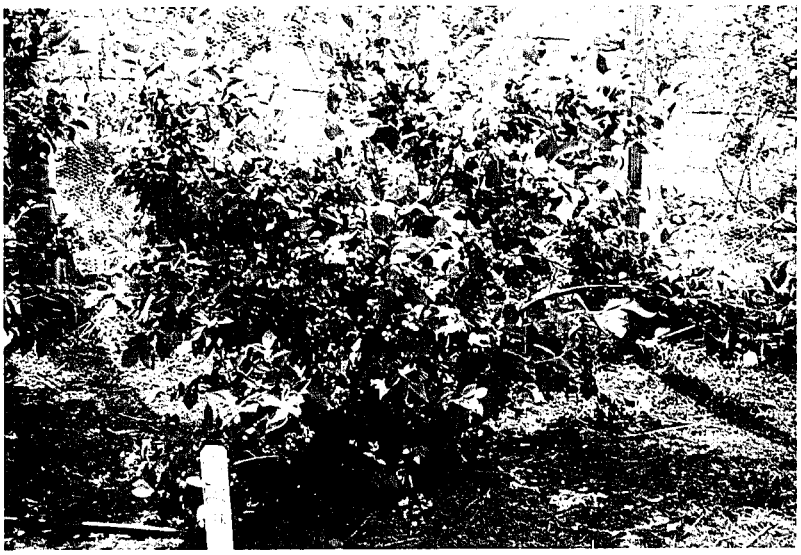
NUI-Bush Habit